United States Patent
Mark

(10) Patent No.: US 10,022,520 B2
(45) Date of Patent: Jul. 17, 2018

(54) SURGICAL ACCESS SYSTEM

(71) Applicant: Nico Corporation, Indianapolis, IN (US)

(72) Inventor: Joseph L. Mark, Indianapolis, IN (US)

(73) Assignee: Nico Corporation, Indianapolis, IN (US)

( * ) Notice: Subject to any disclaimer, the term of this patent is extended or adjusted under 35 U.S.C. 154(b) by 613 days.

(21) Appl. No.: 13/716,622

(22) Filed: Dec. 17, 2012

(65) Prior Publication Data

US 2014/0171873 A1   Jun. 19, 2014

(51) Int. Cl.
| | |
|---|---|
| A61M 25/00 | (2006.01) |
| A61M 25/01 | (2006.01) |
| A61M 29/00 | (2006.01) |
| A61B 17/34 | (2006.01) |
| A61B 34/20 | (2016.01) |

(52) U.S. Cl.
CPC ..... *A61M 25/0102* (2013.01); *A61B 17/3417* (2013.01); *A61B 17/3421* (2013.01); *A61M 29/00* (2013.01); *A61B 2017/347* (2013.01); *A61B 2017/3456* (2013.01); *A61B 2034/2051* (2016.02); *A61M 25/0023* (2013.01); *A61M 2025/0042* (2013.01); *A61M 2210/0693* (2013.01)

(58) Field of Classification Search
CPC ........... A61M 25/0102; A61B 17/3417; A61B 17/3421; A61B 2017/3413
See application file for complete search history.

(56) References Cited

U.S. PATENT DOCUMENTS

| | | |
|---|---|---|
| 3,690,323 A | 9/1972 | Wortman et al. |
| 4,386,602 A | 6/1983 | Sheldon et al. |
| 4,638,798 A | 1/1987 | Shelden et al. |
| 4,798,591 A * | 1/1989 | Okada ........... A61M 25/00 604/170.02 |
| 5,183,464 A | 2/1993 | Dubrul et al. |
| 5,320,611 A | 6/1994 | Bonutti et al. |
| 5,431,676 A | 7/1995 | Dubrul et al. |
| 5,860,996 A | 1/1999 | Urban et al. |
| 6,047,218 A | 4/2000 | Whayne et al. |
| 6,129,685 A | 10/2000 | Howard, III |

(Continued)

FOREIGN PATENT DOCUMENTS

| | | |
|---|---|---|
| RU | 2009124446 A | 1/2011 |
| WO | WO-2007002251 A2 | 1/2007 |
| WO | WO-2008066543 A1 | 6/2008 |

OTHER PUBLICATIONS

A. Schupak, "A Healthy Glow Florescent imaging helps surgeons cut more cancer cells," Poplar Science, Feb. 2011.

(Continued)

*Primary Examiner* — Nathan R Price
*Assistant Examiner* — Justin L Zamory
(74) *Attorney, Agent, or Firm* — Kristin L. Murphy; Brooks Kushman PC

(57) ABSTRACT

A surgical access assembly and method of use is disclosed. The surgical access assembly comprises an outer sheath and an obturator. The outer sheath and obturator are configured to be delivered to an area of interest within the brain. Either the outer sheath or the obturator may be configured to operate with a navigational system to track the location of either device within the brain.

20 Claims, 3 Drawing Sheets

(56) References Cited

U.S. PATENT DOCUMENTS

| | | | |
|---|---|---|---|
| 6,179,826 | B1 | 1/2001 | Aebischer et al. |
| 6,226,548 | B1 | 5/2001 | Foley et al. |
| 6,245,052 | B1 | 6/2001 | Orth et al. |
| 6,280,399 | B1 | 8/2001 | Rossin et al. |
| 6,293,952 | B1 | 9/2001 | Brosens et al. |
| 6,331,180 | B1 | 12/2001 | Cosman et al. |
| 6,374,135 | B1 | 4/2002 | Bucholz |
| 6,416,520 | B1 | 7/2002 | Kynast et al. |
| 6,669,685 | B1 | 12/2003 | Rizoiu et al. |
| 6,942,634 | B2 | 9/2005 | Odland |
| 2003/0045834 | A1* | 3/2003 | Wing ............... A61B 17/34 604/161 |
| 2003/0073934 | A1 | 4/2003 | Putz |
| 2004/0024291 | A1 | 2/2004 | Zinkel |
| 2004/0059375 | A1 | 3/2004 | Ginn et al. |
| 2004/0068172 | A1 | 4/2004 | Nowinski et al. |
| 2004/0102804 | A1 | 5/2004 | Chin |
| 2004/0186346 | A1 | 9/2004 | Smith et al. |
| 2004/0215143 | A1 | 10/2004 | Brady et al. |
| 2007/0270898 | A1 | 11/2007 | Lillehei |
| 2008/0139928 | A1* | 6/2008 | Lubock ............. A61B 19/54 600/414 |
| 2009/0048622 | A1 | 2/2009 | Wilson |
| 2009/0312611 | A1* | 12/2009 | Mangiardi ......... A61B 17/02 600/210 |
| 2010/0010315 | A1 | 1/2010 | Mangiardi |
| 2010/0228084 | A1* | 9/2010 | Sato ................. A61B 8/12 600/106 |

OTHER PUBLICATIONS

Modern Medicine, "New Device May Help Surgeons Resect Brain Tumors," "Fluorescence spectroscopy helps neurosurgeons identify hard-to-see tumor tissue," (Jan 31, 2011).

Nader Sanal, MD, et al., "Intraoperative Confocal Microscopy for Brain Tumors: A Feasibility Analysis in Humans," www.neurosurgery-online.com (Jun. 2011).

Juan C. Fernandez-Miranda, M.D., et al. "High-definition fiber tracking guidance for intraparenchmyal endoscopic port surgery," J. Neurosurg/vol. 113/Nov. 2010.

Manuel Dujovny, et al., "Brain Retractor Systems," Neurological Research, vol. 37, No. 7, (2010).

T. Nakano, et al., "Endoscopic Treatment for Deep-seated or Multiple Intraparenchymal Tumoers: Technical Note," Dept. of Neurosurgery, Hirosaki University Graduate School of Medicine. (2009).

Amin b. Kassam, et al., "Completely endoscopic resection of intraparenchymal brain tumors," J. Neurosurg./ vol. 110/Jan. 2009.

K. Ogura, et al., "Neurosurgical Technique, New microsurgical technique for intraparenchymal lesions of the brain: transcylinder approach," Acta Neurochir (Wien)(2006).

Chun-Chung Chen, M.D., et al., "A stainless steel sheath for endoscopic surgery and its application in surgical evacuation of putaminal haemorrhage," Journal of Clinical Neuroscience (2005).

O. Barlas, et al., Clinical Article, "Stereotactically guided microsurgical removal of colloid cysts," Acta Neurochir (Wien)(2004).

Tetsuhiro Nishihara, M.D., et al., "A transparent sheath for endoscopic surgery and its application in surgical and its application in surgical evacuation of spontaneous intracerebral hematomas," J. Neurosurg/vol. 92/Jun. 2000.

Donald M. O'Rourke, M.D., et al., "Vycor Medical, Inc.—Business Summary," www.vycormedical.com.

Non-Final Office Action dated Nov. 10, 2011 for U.S. Appl. No. 11/665,666.

PCT International Search Report dated Jun. 20, 2006 for PCT/US05/39185.

Wedeen, Van J., et al., "The Geometric Structure of the Brain Fiber Pathways," Science 335, 1628 (2012).

Response to Non-Final Office Action dated Nov. 10, 2011 for U.S. Appl. No. 11/665,666.

Final Office Action dated May 30, 2012 for U.S. Appl. No. 11/665,666.

Response to Final Office Action dated May 30, 2012 for U.S. Appl. No. 11/665,666.

* cited by examiner

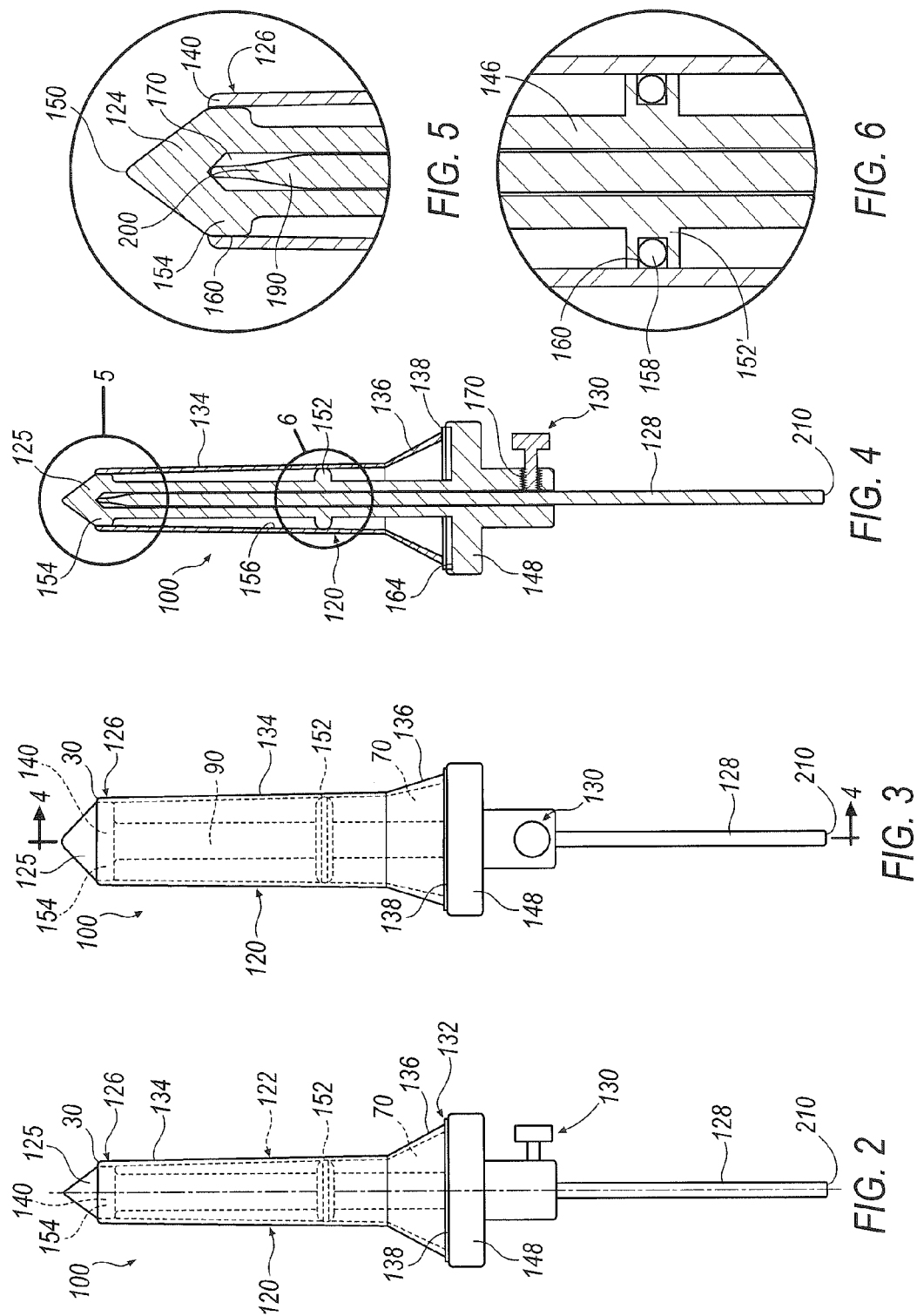

SURGICAL ACCESS SYSTEM

TECHNICAL FIELD

The present disclosure relates generally to a surgical access system for use with delicate and critical tissues, as well as methods of accessing and performing surgery using same.

BACKGROUND

Diagnosis and treatment of conditions affecting the brain are among the most difficult and complex problems that face the medical profession. The brain is a complex and delicate soft multi-component tissue structure that controls bodily functions through a complex neural network connected to the rest of the body through the spinal cord. The brain and spinal cord are contained within and protected by significant bony structures, e.g., the skull and the spine. Given the difficulty of accessing the brain through the hard bony protective skull and the delicate network and complex interactions that form the neural communication network contained within the brain that define the human body's ability to carry on its functions of speech, sight, hearing, functional mobility, reasoning, emotions, respiration and other metabolic functions, the diagnosis and treatment of brain disorders presents unique challenges not encountered elsewhere in the body.

For example, abnormalities such as intracranial cerebral hematomas (ICH), abscesses, glioblastomas (GB), metastases (mets) and functional diseases manifest themselves in the intraparenchymal subcortical space (i.e., the white matter) of the brain are particularly challenging to access, let alone treat. The hemispheres [jm1] of the brain contain eloquent communication structures (neural network) which are located in the subcortical space, called fiber tracts and fascicles. Thus, traditionally, unless the ICH, GB, and/or mets were considered anything but "superficial," such conditions have been considered challenging to access, simply because getting to the abnormality ICH, GB and/or mets are considered just as damaging as letting the condition take its course. Similarly, tissue abnormalities such as tumors, cysts and fibrous membrane growths which manifest within the intraventricular space of the brain are considered challenging to safely access and often inoperable, due to their locations within the brain.

In order to assist in diagnosis and subsequent treatment of brain disorders, clear, accurate imaging of brain tissue through the skull is required. In recent years significant advances have been made in imaging technology, including stereotactic X-ray imaging, Computerized Axial Tomography (CAT), Computerized Tomographic Angiography (CTA), Position Emission Tomography (PET) and Magnetic Resonance Imaging (MRI), Diffusion Tensor Imaging (DTI) and Navigation systems (instrument position tracking systems). These imaging devices and techniques permit the surgeon to observe conditions within the brain in a non-invasive manner without opening the skull, as well as provide a map of critical structures surrounding an area of interest, including structures such as blood vessels, membranes, tumor margins, cranial nerves, including fiber tracts and fascicles. If an abnormality is identified through the use of one or more imaging modalities and/or techniques, it may be necessary or desirable to biopsy or remove the abnormality.

Once a course of action has been determined based upon one or more imaging techniques, a surgical treatment may be necessary or desired. In order to operate surgically on the brain, access must be obtained through the skull and delicate brain tissue containing blood vessels and nerves that can be adversely affected by even slight disturbances. Therefore, great care must be taken in operating on the brain so as not to disturb delicate blood vessels and nerves to prevent adverse consequences resulting from a surgical intervention.

Traditionally, accessing abnormalities which manifest in deeper spaces within the brain has meant a need for a surgery that creates a highly invasive approach. In some instances, in order to obtain access to target tissue, a substantial portion of the skull is removed and entire sections of the brain are retracted to obtain access. Such technique is referred to as an "open" procedure. For example, traditional surgical brain retractors are metal bands, with abrupt or well-defined edges and have limited surface areas. These traditional surgical brain retractors are used to pull apart or spread delicate brain tissue, which can leave pressure marks from lateral edges of the retractor, indicating high local compression stress. In some instances, a complication known as "retraction injury" may occur due to use of brain retractors. Further, brain tissue can be torn by the relatively sharp edges of the retractors. In addition, the retracted brain tissue can lose blood supply if the localized pressure of the retractors is greater than the venous pressure, which can lead to ischemic changes. Of course, such "open" techniques are not appropriate for all situations, and not all patients are able to tolerate and recover from such invasive techniques.

It is also known to access certain portions of the brain by creating a burr hole craniotomy, but only limited surgical techniques may be performed through such smaller openings. In addition, some techniques have been developed to enter through the nasal passages, opening an access hole through the occipital bone to remove tumors located, for example, in the area of the pituitary.

A significant advance in brain surgery is stereotactic surgery involving a stereotactic frame correlated to stereotactic X-ray images to guide a navigational system probe or other surgical instrument through an opening formed in the skull through brain tissue to a target lesion or other body. A related advance is frameless image guidance, in which an image of the surgical instrument is superimposed on a pre-operative image to demonstrate the location of the instrument to the surgeon and trajectory of further movement of the probe or instrument. However, once the navigational system probe is removed, information concerning the location of any retractors or other surgical instruments that may be used during procedures is unavailable.

In recent years, surgical access systems have been developed to provide access to previously difficult to access areas. One such prior art system is shown in FIGS. 1A-1C. System 10 includes a retractor 20 and an introducer 40. Retractor 20 has a hollow working channel and is generally shorter than introducer 40. Retractor 20 is configured as a hollow elliptical rounded wedge. Introducer 40 is also hollow and includes a cone-shaped distal end 42 with an opening 52 therein (best seen in FIG. 1C). The cone-shaped distal end is configured to be a generally blunt, flat surface. With introducer 40 positioned within retractor 10, system 10 is inserted into brain tissue, thereby pushing brain tissue away while providing access to an area of interest. Once system 10 is delivered to the area of interest, retractor 10 is rigidly fixed in position. More specifically, retractor 10 is fixed in space with the use of a standard or conventional neurosurgical fixation device. Once retractor 10 is fixed in place, introducer 40 is then removed from retractor 10, while leaving retractor 10 in its fixed place, thereby creating a pathway through the brain tissue. However, no mechanism for providing navigational information concerning the retractor 10 with respect to the patient's anatomy is provided.

While access system 10 may provide a manner to access certain brain tissue, however due the blunt nature of the tip configuration of the inner sheath the cortex must first be opened via a cortisectomy or corticotomy with the use of knife which is traumatic to the cortex and requires the removal of blood vessels on the cortex which provide both the cortex with nutrients and drainage for the elimination of waste products. This is also true of the underlying white matter, which must also be cut to create a space for the device to be inserted, so as to not displace the white matter and cause brain shift or pressure via restrictions on the surrounding eloquent fiber tracts. Therefore, if an opening and pathway are not created for the blunt shaped distal end of the device, it can actually cause transient or even permanent deformation and trauma of delicate tissue structures which can manifest itself in temporary or permanent neurological deficits after surgical cytoreduction due to damage of blood vessels, cranial nerves, fiber tracts and fascicles. Opening 52 may cause coring of tissue, also leading to damage of the tissues and structures as introducer 40 is pushed through tissue. Further, by rigidly fixing the placement of retractor 10, manipulation of retractor 10 is impeded and requires constant attention by loosening and retightening to re-position for even micro-movement of the retractor 10, without critical information concerning surrounding structures in relation to the retractor 10 available, thereby lengthening procedure time.

Thus, there exists a need for improved surgical access system that reduces potential damage to brain tissue and structures, as well as providing navigational capabilities for the access system.

BRIEF DESCRIPTION OF THE DRAWINGS

Exemplary embodiments of the present disclosure will now be described in greater detail with reference to the attached figures, in which:

FIG. 2 is a first side elevational view of an assembled surgical access system;

FIG. 3 is a second side elevational view of the surgical access system of FIG. 2, rotated 90°;

FIG. 4 is a cross-sectional view of the assembled surgical access system of FIGS. 2-3, taken along lines 4-4 in FIG. 3;

FIG. 5 is an enlarged view of encircled area 5 in FIG. 4;

FIG. 6 is an enlarged view of an alternative configuration for encircled area 6 in FIG. 4.

DETAILED DESCRIPTION

Figure 1A:
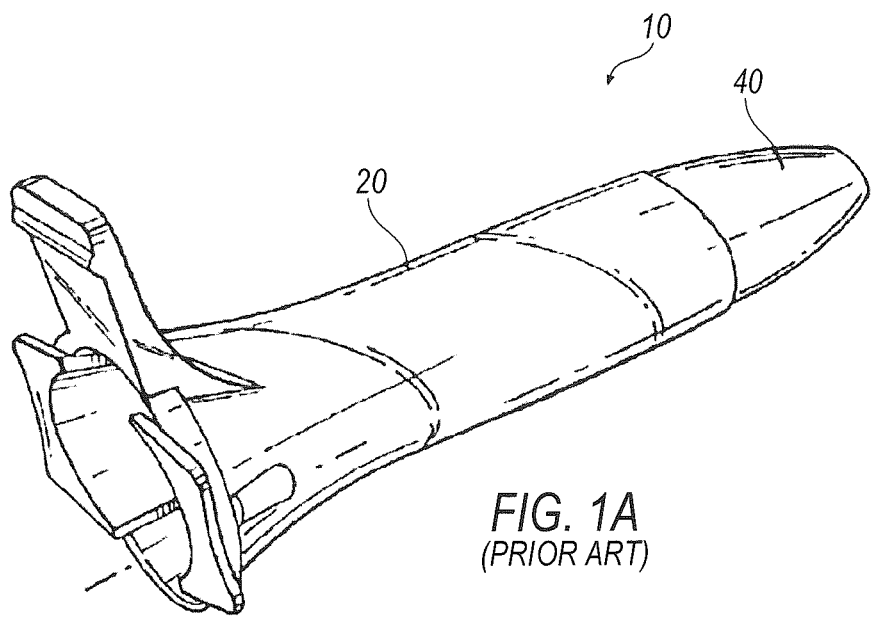
FIGS. 1A-1C illustrate a prior art surgical access system.

Referring now to the discussion that follows and also to the drawings, illustrative approaches to the disclosed assemblies and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein is surgical access assembly, various components for use in same, and a method of using the surgical access assembly. The components disclosed herein provide surgeons with an enhanced ability to minimize trauma to the patient, while providing efficient improved minimally invasive surgical techniques, such as, for example, during intracranial surgical techniques. The components disclosed herein may further be used for application of targeted and effective treatment regimens.

Referring to FIGS. 2-6, a surgical access assembly 100 is shown. In one exemplary arrangement, surgical access assembly 100 comprises a hollow outer sheath 120 and a selectively removable obturator 122. Obturator 122 is configured with a length that is longer than a length of outer sheath 120 such that a distal end 124 of obturator 122 protrudes a predetermined distance from a distal end 126 outer sheath 120, when obturator 122 is attached to outer sheath 120, as will be discussed below in greater detail.

A navigation probe 128 may also be included as part of surgical access assembly 100. Navigation probe 128 is configured to be inserted within obturator 122, as will be explained below in further detail. A locking member 130 may also be provided. Locking member 130 is configured to operatively retain navigation probe 128 within obturator 122.

Outer sheath 120 is defined by distal end 126 and a proximal end 132. Outer sheath 120 includes a generally hollow body portion 134 and a connector portion 136. In one exemplary arrangement, connector portion 136 is configured to flare outwardly toward the proximal end 132. In one exemplary arrangement, proximal end 132 is configured with a mounting flange 138.

In one exemplary arrangement, at least body portion 134 is constructed of a clear biocompatible material that permits viewing of normal tissue, abnormal tissue, as well as critical structures that are disposed outside of body portion 134 when outer sheath 120 is disposed within such tissue. In one exemplary arrangement, outer sheath 102 is constructed of polycarbonate, though other biocompatible materials may be employed, including resins.

In one exemplary arrangement, body portion 134 of outer sheath 120 is configured with a non-circular cross-section, such as an elliptical configuration. However, the disclosure is not limited to such a configuration. Further, body portion 134 may be configured to taper from proximal end 132 to distal end 126, although the disclosure is no so limited. Alternatively, distal end 126 of outer sheath 120 may be configured with a separate tapered portion (not shown) that extends towards a center axis of outer sheath 120. A distal edge 140 (best seen in FIG. 5) surrounds an opening 142 in distal end 126 of outer sheath 120. Distal edge 140 may be configured with a slight inward taper to ease the transition between distal end 126 of outer sheath 120 and a distal tip portion 124 of obturator 122, without drag, trauma or coring of tissue.

In one exemplary configuration, distal edge 140 may be configured with a radius or other configuration so as to be non-sharpened so as to create a smooth/atraumatic transition of the brain tissue when surgical access assembly 100 is inserted into the brain, as will be explained below in further detail.

Obturator 122 is defined by a distal end 124 and a proximal end 144. A body portion 146 extends therebetween. A handle portion 148 may be provided, as well. Distal end 124 is configured with a generally conical shaped distal tip portion 125 that tapers to a tip member 150 to provide atraumatic dilation of tissue. In one exemplary arrangement, tip portion 125 tapers toward a closed tip member 150 so as to prevent coring of tissue as obturator 122 is inserted into the brain.

In one exemplary arrangement, tip portion 125 is radiused, best shown in FIG. 5, to assist in atraumatically move tissue, as well as other structures within the brain, including white matter, away from outer sheath 120, as surgical access system 100 is inserted into the brain, but without cutting tissue or such structures. Indeed, unlike prior art devices that include either a blunt tip distal end or a tapered leading edge such as that shown in FIG. 1C, radiused distal tip 150 cooperates with distal edge 140 and obturator 122 to prevent bruising and damage to various tissue. More specifically, this configuration facilitates entry of outer sheath 120 into delicate tissue, but without cutting such delicate tissue. Insertion of surgical access assembly 100 will be explained in further detail below.

Obturator 122 further includes one or more alignment ribs 152, 154 to facilitate proper mating of obturator 122 with outer sheath 120. Alignment rib 152 is disposed about a body portion 146. While shown positioned closer to proximal end 144 of obturator 122 than distal end 124, alignment rib 152 may be disposed anywhere along body portion 146. Alignment rib 152 may be fabricated of a flexible material that is configured to conform to the inner surface 156 of outer sheath 120, such that obturator 122 may be used with a variety of different outer sheaths 120, including outer sheaths 120 having circular cross-sections, as well as those having a non-circular cross-section, such as an elliptical cross-section. In one exemplary arrangement, alignment rib 152 may be overmolded to body portion 146 such that alignment rib 152 is integral with obturator 122.

In another exemplary arrangement, best seen in FIG. 6, alignment rib 152 may be integrally formed with obturator 122, including the same material as body portion 146. A separate sealing member 158 is provided and arranged to be disposed within a sealing groove 160 formed within alignment rib 152'.

A second alignment rib 154 may be provided adjacent tip portion 125, as best seen in FIG. 5. Second alignment rib 154 is configured to provide proper fit and a smooth transition between outer sheath 120 and obturator 122 so as to prevent tissue damage as surgical access assembly 100 is inserted into tissue. In one exemplary arrangement, second alignment rib 154 is configured with a land area 160 that is configured to engage inner surface 156 of outer sheath 120, adjacent distal end 126. In one exemplary arrangement, second alignment rib 154 is configured with a compressible material to permit second alignment rib 154 to conform to the cross-section of distal end 126 of obturator 120.

Figure 1B:
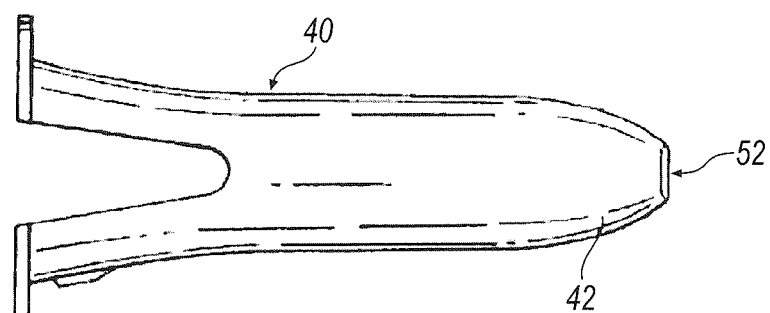
Figure 1C:
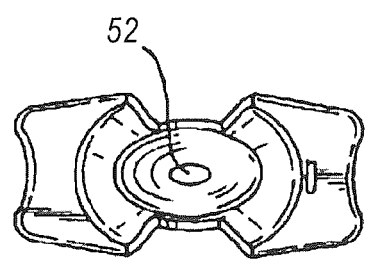

Handle portion 148 is disposed adjacent proximal end 144. In one exemplary arrangement, handle portion 148 is configured as a flange member that extends around the outer periphery 162 of obturator 122. While illustrated as extending completely around outer periphery 162, it is understood that handle portion 148 may be constructed of one or more different segment such that the flange member is discontinuous, similar to what is shown in FIGS. 1A-1C.

Figure 7:
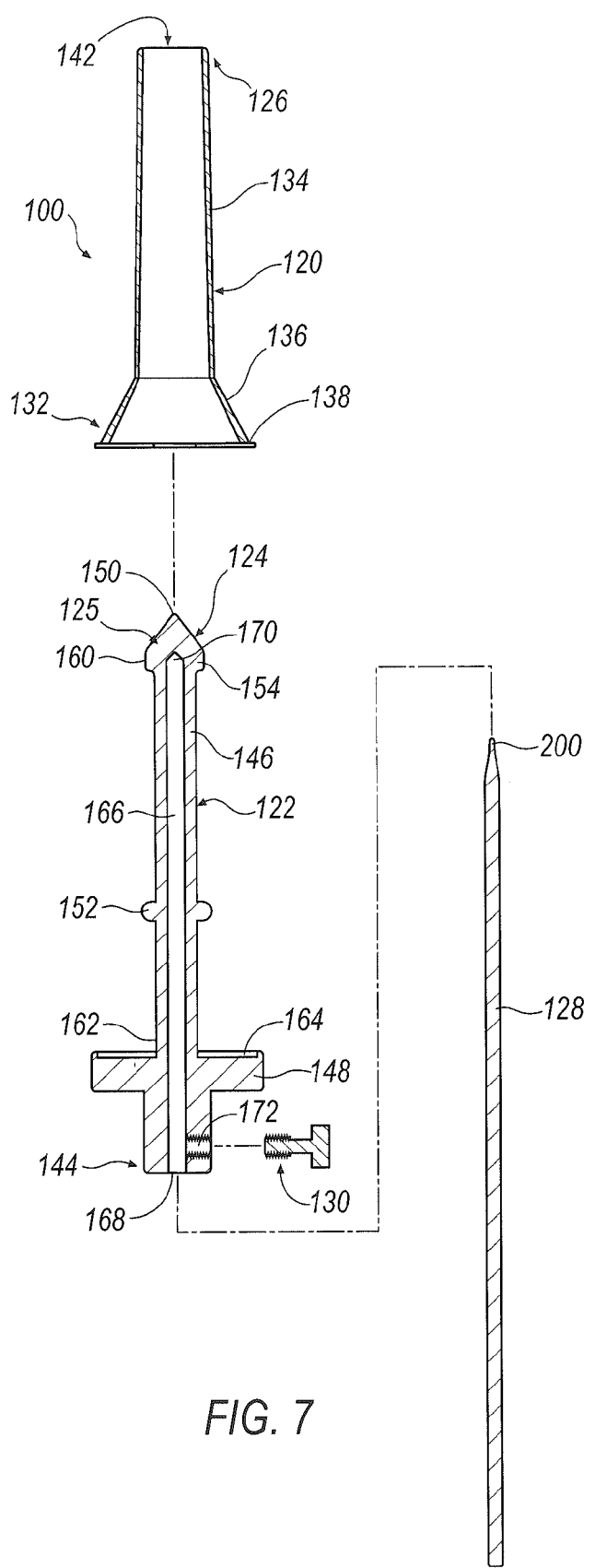
FIG. 7 is a cross-sectional exploded view of the surgical access system of FIGS. 2-5.

In one exemplary arrangement, flange member of handle portion 148 may further be configured with at least a partial mounting groove 164 (best seen in FIG. 7). Mounting groove 164 is configured to receive proximal end 132 of outer sheath 120 so as to engage obturator 122 to outer sheath 120. More specifically, as discussed above, proximal end 132 may be configured with a mounting flange 138 that is received within mounting groove 164 of handle portion 148. Other known arrangements for connecting outer sheath 120 to obturator 122 are also contemplated.

Obturator 122 may also be configured with a channel 166 (best seen in FIG. 7) that is configured to receive navigation probe 128. Channel 166 is defined by a proximal opening 168 and extends toward distal end 124, terminating in a closed pocket 170. More specifically, pocket 170 is defined by a distal end of channel 166 converging to form an apex that is configured to seat a distal tip 200 of navigation probe 128 at a fixed offset from distal tip 150 of obturator 122. With this configuration, pocket 170 is also configured so as to align distal tip 200 of navigation probe 128 with distal end 126 of outer sheath 120, when outer sheath 120 is assembled to obturator 122 (as best seen in FIG. 5).

To secure navigation probe 128 to obturator 122, locking member 130 may be provided. In one exemplary configuration, locking member 130 is constructed as a threaded fastener that engages with a receiving aperture 172. Receiving aperture 172 is in communication with channel 166 such that when navigation probe 128 is mounted within channel 166, locking member 130 frictionally engages navigation probe 128.

In another exemplary arrangement outer sheath 120 may also be (or alternatively be) provided navigational capabilities that permit a user to "read" the location of outer shaft 120 after placement at an area of interest, as well as update the location of outer sheath 120 during a procedure. In one exemplary arrangement, an RFID chip or sensor that is configured to be tracked by a navigation system, may be incorporated into outer sheath 120. For example, an RFID chip or sensor may be permanently attached to outer sheath 120, for example, by impregnating or molding the RFID chip or sensor therein. In other exemplary arrangements, a temporary sensor or chip may be incorporated into or attached to outer sheath 120. For example, outer sheath 120 may be provided with one or more channels within the wall that defines outer sheath 120. An RFID chip and/or sensor may be positioned within the channels. Alternatively, the RFID chip and/or sensor may be positioned within mounting flange 138.

There are a number of variables that play the selection of the angle α that defines the taper of tip portion 125 of obturator 122. These variables include the size of an outer diameter D1 of obturator 122, the desired length that distal tip portion 125 extends from body portion 146, and the desired offset for distal tip 200 of navigation probe 128 and tip member 150. More specifically, it is contemplated that surgical access assembly 100 will be provided as part of a kit that may include multiple sized outer sheaths 120 and obturators 122, to provide the surgeon with a choice of different diameter sizes and lengths so as to provide flexibility for accessing areas of interest within the brain. However, to insure that the distal tip 150 is determinable regardless of which size diameter D1 of obturator 122 is used, taper angle α may be selectively adjusted. For embodiments that utilize navigation probe 128 that positions a distal end thereof at a set position within obturator 122 (as will be explained in further detail below), to maintain an identical offset length between the distal end of navigation probe 128 and distal tip 150 in different diameter D1 sized obturators 122, taper angle α will need to be increased, as diameter D1 increases to achieve atraumatic dilation, as well as a determinable distal tip 125 location.

As best seen in FIG. 5, distal tip 125 is configured to be radiused such that tip member 150 is rounded, and neither blunt, nor sharp. More specifically, tip member 150 is configured so as not to have any flat portions which during insertion can stretch or even tear the delicate tissues such as the vessels, fiber tracts and fascicles found in the brain. Further, because tip member 150 is closed, damage of such delicate tissues and fascicles are also avoided. In one exemplary embodiment, tip member 150 is configured with a 0.5 mm radius. The configuration of tip member 150 is designed to gently displace and move the tissue into which it is inserted; i.e., atraumatically dilate the tissue to allow for introduction in to an intra-fascilar and para-fascilar manner, as opposed to cutting tissue as surgical access assembly 100 is inserted into the tissue.

Operation of surgical access assembly will now be described. Once an area of interest in the brain is determined, an additional imaging sequence may be employed to determine the location of eloquent structures such as vessels and fiber tracts and the associated fascicles so as to plan the safest access route to the area of interest. Exemplary arrangements for accomplishing this step include CT-Angiography and MRI with Diffusion Tensor Imaging (DTI) sequences. DTI allows for the determination of directionality as well as the magnitude of water diffusion along the communication "wiring" pathways called fiber tracts and fascicles. This kind of MRI imaging can provide imaging to allow for the estimation of potential damage to nerve fibers that connect the areas of the brain which can be affected by a stroke, for example, to brain regions that are distant from it, and can also be used to visualize white matter fibers in the brain and can map (trace image) subtle changes in the white matter associated with diseases such as multiple sclerosis and epilepsy, as well as assessing diseases where the brain's wiring is abnormal, such as schizophrenia, as well as tumor involvement.

Diffusion Tensor Tractography (DTT) may also be used. DTT allows for noninvasive racking of neuronal fiber projections in a living human brain. White matter fiber trajectories are reconstructed throughout the brain by tracking the direction of fastest diffusion, which is assumed to correspond to the longitudinal axis of the tract. Diffusion tensor tractography provides insight into white matter integrity, fiber connectivity, surgical planning, and patients' prognosis. Once the imaging information has been analyzed, valuable information about potential avenues for access tracts to and area of interest will be determined.

Next, a plan for the operative trajectory is developed. More specifically, imaging information is used to plan (either manually or with software) the access tract/pathway to achieve fiber tract involvement during access to the area of interest. In evaluating fiber tract involvement from a potential access tract/pathway, consideration of fiber tract importance may be based on an individual patient's occupational and personal needs and/or preference.

Next, image data from the MRI/DTI and CT/CTA image sequence may be input into an intraoperative navigation system. Intraoperative navigation systems may be used to provide direct visualization of an area of interest in real time, as surgical access system 100 is being positioned within the brain.

After the appropriate surgical plan is developed, the surgeon begins a surgical procedure by creating access to the area of interest. For brain surgery, the surgeon creates the craniotomy and Dural access incision.

Next, the obturator 122 is inserted into outer sheath 120 until mounting flange 138 is seated within mounting groove 164, as shown, for example, in FIG. 4. Navigation probe 128 is then inserted into channel 166 until distal tip 200 is seated within pocket 170. With distal tip 200 of navigation probe 128 positioned within pocket 170, distal tip 200 of navigation probe 128 will be positioned within the same plane as distal tip 140 of outer sheath 120, when obturator 122 and outer sheath 120 are assembled together as shown in FIGS. 1-4. Locking member 130 may be tightened to fixedly retain navigation probe 128 within obturator 122.

A portion of navigation member 128 will extend proximally from obturator 122 and will be operatively connected to a navigation system in a known manner, such system including a screen that visually illustrates the information obtained from the imaging sequences, along with the trajectory of surgical access system 100. Thus, with the navigation probe 128 operatively connected to a navigation system, the position of distal tip 140 of outer sheath may be indicated, in real time, while surgical access system 100 is being navigated within a body.

In another configuration, the software operating the navigation system may further be provided with an offset dimension that corresponds to a distance between distal tip 150 of obturator 122 and distal tip 140 of outer sheath 120. In this arrangement, a dotted line may appear on the navigation screen that indicates where distal tip 150 of obturator 122 is located, in real-time.

Navigation probe 128 may further be provided with image guidance position indicators, such as an array of reflectors of the type use in connection with optical image guidance systems. The infrared reflectors used with such a system are mounted to a handle of a probe-like navigation probe 128 in a customary triangular configuration calibrated to identify the tool to the image guidance system. Such imaging systems are available, for example Medtronic Surgical Navigation Technologies (Denver, Colo.), Stryker (Kalamazoo, Mich.), and Radionics (Burlington Mass.).

Typically, the positioning of the indicators is calibrated such that the image guidance system can project an image of the tool onto a display of images of the patient's brain, such as MRI images used to plan surgery. Thus, as discussed above, as surgical access system 100 is inserted, the surgeon can see the relative position of system 100 relative to the structures of the brain as reflected on images, and particularly with respect to the target tissue.

Other guidance systems, such as magnetic or electromagnetic or radio transmitting systems may also be used, and the illustration of infrared reflectors and discussion of optical image guidance systems are exemplary only and are not intended to be limiting. In addition, while the exemplary method has been described in connection with superimposing an image of surgical access system 100 onto a preoperative image, it is contemplated that real-time imaging capability may be utilized and that the image of surgical access system 100 may then be shown in relation to the surrounding tissue structures on a real time image.

In another exemplary configuration, an RFID chip may be embedded in obturator 104 that operatively communicates information to a navigation system or other surgical system about the specific attributes, such as, but not limited to, length and diameter. This information may be used to facilitate placement with the navigation system or other systems for information display or trajectory and location calculations during placement of obturator 122.

Once surgical access assembly 100 is assembled and operatively connected to a navigational system, the surgical access assembly 100 is then navigated to an area of interest. In one exemplary arrangement, distal tip 150 of obturator 122 is directed to a furthermost outer margin of an area of interest. Due to the tapered configuration and closed, radiused distal tip 150 of obturator 122, as well as the radiused distal tip 140 of outer sheath 120, as surgical access assembly 100 is inserted into the brain and navigated to the area of interest, tissue is gently pushed to either side of surgical access assembly 100, so as to atraumatically dilate tissue, while minimizing trauma to the tissue. Further, because surgical access assembly 100 is operatively connected to navigation probe 128, as surgical access assembly 100 is being inserted into the brain tissue, navigation probe 128 may cooperate with an imaging modality to providing real-time information concerning fiber tact in a trajectory, thereby allowing the surgeon to minimize fiber tract compromise or damage during insertion of surgical access assembly 100.

Once surgical access assembly 100 is positioned at the area of interest, the navigation probe 128 may be removed from or detached from surgical access assembly 100. Once navigation probe 128 is removed, outer sheath 120 is then operatively positioned with respect to the area of interest. More specifically, outer sheath 120 is decanted with respect to obturator 122 such that distal end 140 of outer sheath 120 is moved toward distal end 124 of obturator 122. This action is accomplished by grasping mounting flange 138 with one hand while maintaining obturator 122 stationary, such, for example, grasping handle member 148 with another hand. Mounting flange 138 may be gently rotated and/or swiveled with respect to a central axis of obturator 122 to enable outer sheath 120 to be moved distally with respect to obturator 122. Outer sheath 120 is decanted a distance that generally corresponds to the length of distal tip portion 124 of obturator 122. In one exemplary arrangement, an indicator may be provided on outer surface 162 of obturator 122 such that when mounting flange 138 is decanted sufficiently to align with the indicator, the distal end 140 of outer sheath 120 is aligned tip member 150 of obturator 122. Moreover, once so decanted, outer sheath 120 is positioned within the area of interest.

Once outer sheath 120 is appropriately positioned, obturator 122 is then removed from outer sheath 120. More specifically, outer sheath 120 is maintained to be relatively stationary at the area of interest, and obturator 122 is moved in a proximal direction until fully removed from outer sheath 120. This action results in outer sheath 120 forming a pathway to the area of interest 500 that provides direct access to the area of interest within the patient.

In other embodiments, rather than provide obturator 122 with navigation probe 128, or in addition to providing obturator 122 with navigation probe 128, as discussed above, outer sheath 120 may be provided with and RFID chip or sensor. With this configuration, the RFID chip or sensor of outer sheath 120 cooperates with the navigation system thereby making outer sheath 120 visible to the user on the navigation system, independent of obturator 122. Thus, once obturator 122 is removed from outer sheath 120, the location within the patient of outer sheath 120 will still be visible to the navigation system.

More specifically, the navigation system works with the additional images taken during the imaging sequence. The images are uploaded into the intraoperative navigation system. The RFID chip and/or sensors are configured to be read by the navigation system and place an image of outer cannula 120, thereby allowing the surgeon to direct visualize the location of outer cannula 120, while positioned within the patient.

Once outer sheath 120 is placed in its desired location, outer sheath 120 may then secured in place so as to prevent cranial pressure or general manipulation of instruments passing in and out of the sheath 120 from pushing or dislocating outer sheath 120 out of the brain tissue, in any known manner. Once outer sheath 120 is secured, surgical intervention or therapy may be undertaken at the area of interest.

After surgery and therapy on the target tissue is complete, the instruments used for surgery and/or therapy are removed from outer sheath 120. As the target tissue is removed, brain tissue will naturally fill the void formed by removing the area of interest so that healthy brain tissue underlying the now removed target tissue is adjacent the end of outer sheath 120. Outer sheath 120 is then gently removed and the brain tissue will naturally fill and reclaim the space formerly occupied by the abnormality and outer sheath 120, which may be aided by irrigation of the area of interest. Once outer sheath 120 has been removed, the dura, skull and scalp are then closed in a known manner and the process ends.

Because the location of the area of interest will vary from patient to patient, in one exemplary arrangement, it is contemplated that surgical access system 100 will be provided as part of a kit. More specifically, it is contemplated that a set of multiple obturators 122 may be provided that have different lengths and/or diameters. The set may be provided in a container that is configured be sterilized, with obturators 122 secured therein. Outer sheath 120 may be provided with the kit, in various lengths and diameters that correspond to the lengths and diameters of obturators 122 provided in the kit. However, in one exemplary arrangement, outer sheaths 120 are provided separately as single use devices, in sterilized pouches.

While the above-described system provides the advantage of creating direct access to an area of interest, including an area of interest in the subcortical space, thereby permitting debulking of the area of interest to reduce the biological load of the abnormal tissue, as well as delivery of therapy in-situ (without the encumbrance and limitations encountered with systemic therapy delivery), for certain diseases, additional subsequent therapy may be warranted for increased therapeutic benefits.

It will be appreciated that the surgical access system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A medical device for creating access into the soft tissue of the brain or spine, comprising:
   a sheath defined by an open distal end, an open proximal end, a lumen located between the open distal and proximal ends;
   an obturator having a distal end portion, a proximal end portion and a body portion therebetween, the obturator insertable within the sheath to an introducing configuration, whereby the distal end portion extends outside the open distal end of the sheath; and
   a navigation element configured to be disposed within the sheath, and configured to be coupled to at least one of the sheath and the obturator, wherein a distal end of the navigational element does not extend past the open distal end of the sheath when the navigation element is disposed within the sheath in the introducing configuration, and wherein a portion of the navigation element extends proximally from the obturator and is configured to be coupled to a navigation system to indicate the position of the sheath within a body.

2. The medical device of claim 1, wherein the sheath further includes a base portion positioned adjacent the proximal end of the sheath, wherein the base portion is defined by a proximal opening periphery that is sized to be larger than a periphery of the lumen.

3. The medical device of claim 1, further comprising a rim adjacent the proximal opening of the base portion.

4. The medical device of claim 1, wherein the obturator further comprises a stop member that is sized to be larger than the proximal end of the sheath.

5. The medical device of claim 4, wherein the stop member further comprises a groove formed on a distal facing surface of the stop member, wherein the groove is configured to receive a portion of the proximal end of the sheath.

6. The medical device of claim 1, wherein the obturator further comprises at least one rib member disposed about a periphery of the body portion of the obturator, the rib having a cross-sectional thickness greater than a cross-sectional thickness of a wall member that defines the body portion, wherein the rib is sized to be received within the sheath.

7. The medical device of claim 1, wherein the navigational element is a probe configured to be operatively connected to an imaging system, wherein the probe is configured to be connected to the obturator.

8. The medical device of claim 7, wherein the probe is defined with a tip projection that is configured to seat within the obturator.

9. The medical device of claim 7, further comprising a securing mechanism configured to operatively fix the probe to the medical device.

10. The medical device of claim 9, wherein the securing mechanism comprises a bore member arranged adjacent a proximal end of the obturator, wherein the bore opens into a channel within the obturator, and wherein the bore is configured to receive a fastening mechanism that engages a portion of the probe when the probe is arranged in the channel.

11. The medical device of claim 1, wherein the obturator is configured with a tip member that has a base portion that is defined by a cross-section that is greater than a cross-section of the open distal end of the sheath.

12. The medical device of claim 11, wherein the tip member is contoured to a narrow distal end tip.

13. The medical device of claim 11, wherein the tip member is contoured to a narrow closed distal end tip.

14. The medical device of claim 12, wherein the distal end tip is blunt.

15. The medical device of claim 12, wherein the distal end tip is sharp.

16. The medical device of claim 12 wherein the distal end tip is atraumatic.

17. The device of claim 1, wherein the sheath is configured with a non-circular cross-section.

18. The device of claim 1, wherein the obturator is configured with a non-circular cross-section.

19. The device of claim 1, wherein the sheath is configured to be transparent.

20. A medical device for creating access into the soft tissue of the brain or spine, comprising:
    a sheath defined by an open distal end, an open proximal end, a lumen located between the open distal and proximal ends;
    an obturator having a distal end portion, a proximal end portion and a body portion therebetween, the obturator insertable within the sheath to an introducing configuration, whereby the distal end portion extends outside the open distal end of the sheath;
    wherein the obturator further comprises a channel that terminates in a closed pocket that is offset from a distal tip of the obturator, the closed pocket being defined by converging planar surfaces that form an apex; and
    a navigation element configured to be coupled to at least one of the sheath and the obturator, the navigation element having a distal tip that seats within apex of the closed pocket.

* * * * *